(12) United States Patent
Park et al.

(10) Patent No.: US 9,296,684 B2
(45) Date of Patent: Mar. 29, 2016

(54) ALLYL 2-CYANOACRYLATE PREPOLYMER, PREPARATION METHOD THEREOF, AND BIOADHESIVE COMPOSITION COMPRISING THE PREPOLYMER

(71) Applicant: UNIVERSITY-INDUSTRY COOPERATION GROUP OF KYUNG HEE UNIVERSITY, Yongin-si, Gyeonggi-do (KR)

(72) Inventors: Hun Kuk Park, Seoul (KR); Jin Ik Lim, Seoul (KR); Ji Hye Kim, Seoul (KR)

(73) Assignee: UNIVERSITY-INDUSTRY COOPERATION GROUP OF KYUNG HEE UNIVERSITY (KR)

( * ) Notice: Subject to any disclaimer, the term of this patent is extended or adjusted under 35 U.S.C. 154(b) by 257 days.

(21) Appl. No.: 13/670,277

(22) Filed: Nov. 6, 2012

(65) Prior Publication Data

US 2013/0116465 A1  May 9, 2013

(30) Foreign Application Priority Data

Nov. 7, 2011 (KR) .......................... 10-2011-0115354

(51) Int. Cl.
*C07C 255/23* (2006.01)
*C07C 253/30* (2006.01)

(52) U.S. Cl.
CPC .................................... *C07C 255/23* (2013.01)

(58) Field of Classification Search
None
See application file for complete search history.

(56) References Cited

U.S. PATENT DOCUMENTS 3,825,580 A * 7/1974 Kato et al. ..................... 558/443
4,013,703 A   3/1977 Buck

OTHER PUBLICATIONS

First Office Action issued in Korean Patent Application No. 10-2011-0115354 on Apr. 9, 2013.
Klemarcyzk, "A general synthesis of 1,1 disubstituted electron deficient olefins and their polymer properties", Polymer, 1998, vol. 39(1), pp. 173-181(1998).

* cited by examiner

*Primary Examiner* — Alicia L Otton
(74) *Attorney, Agent, or Firm* — Joseph R. Baker, Jr.; Gavrilovich, Dodd & Lindsey LLP

(57) ABSTRACT

An allyl 2-cyanoacrylate prepolymer, a preparation method thereof, and a bioadhesive composition including the prepolymer thus produced are provided, and more particularly, an allyl 2-cyanoacrylate prepolymer having a structure, in which at least one double bond in a molecule remains at an adjacent site to a cyano group prepared by causing a prepolymerization in a double bond moiety of an allyl group by pre-polymerizing through heating 2-cyanoacrylate having at least two double bonds in a molecule such as allyl 2-cyanoacrylate, a method for preparing the same, and a bioadhesive composition including the prepolymer thus produced are provided.

8 Claims, 3 Drawing Sheets

ALLYL 2-CYANOACRYLATE PREPOLYMER, PREPARATION METHOD THEREOF, AND BIOADHESIVE COMPOSITION COMPRISING THE PREPOLYMER

CROSS REFERENCE TO RELATED APPLICATIONS

This application claims priority under 35 U.S.C. §119 from Korean Application Serial No. 10-2011-0115354, filed Nov. 7, 2011, the disclosure of which is incorporated herein by reference.

FIELD OF THE INVENTION

The present invention relates to an allyl 2-cyanoacrylate prepolymer, a preparation method thereof, and a bioadhesive composition including the prepolymer thus produced, and more particularly, to an allyl 2-cyanoacrylate prepolymer having a structure in which at least one double bond in a molecule remains at a site adjacent to a cyano group prepared by causing prepolymerization in a double bond moiety of an allyl group by pre-polymerizing heating 2-cyanoacrylate having at least two double bonds in a molecule such as an allyl 2-cyanoacrylate, a method for preparing the same, and a bioadhesive composition including the prepolymer thus produced.

BACKGROUND

Medical operations for the purpose of aesthetic effect and products associated with said operations are being researched and announced every day, especially in the field of surgical treatment. In the past, the general trend consisted of a method or product in which technical and aesthetic factors were separate from each other, but recently, the treatment methods of a more advanced type having a combination of technical and aesthetic factors tend to be preferred. As the most widely used technique, a suture is performed as a final step upon a skin incision resulting from a surgical operation, accident, or the like, regardless of the size of the incision.

Generally, a nondegradable or biodegradable suture thread is used but this can cause many problems. First, the larger the affected area, the longer the length of suture thread required and the larger the number of suture stitches on skin. Accordingly, it is not preferred from an aesthetic point of view. In addition, a bandage is applied to the affected area that must frequently be changed, which causes discomfort. A still larger problem is that scars may remain from the area corresponding to the suture thread. Moreover, patients are reluctant to use this method in the case of exposed body parts, such as the face, hands and legs, and additionally this may lead to an unavoidable second operation for removing any scars.

In order to address the problems described above, it is known that several products alternative to the suture thread are being sold and used in and around certain large hospitals. A cyanoacrylate adhesive, a fibrin glue, a gelatin glue, and a urethane-based adhesive are representative, and as the cyanoacrylates among them, an octyl 2-cyanoacrylate (Dermabond®) and an N-butyl 2-cyanoacrylate (Histoacryl®) are finished products imported from the US or Germany and are currently available on the market. Unfortunately, they have issues in that the polyalkylcyanoacrylate after polymerization has a hard physical property through a rapid reaction rate with water and properties of cyanoacrylate such that it can be while applied to living body tissues, patients often complain of discomfort, general dislike, and the like due to difference in the physical properties of soft skin area, after operation and cracks or partial albinism has been often caused due to a weakness in absorptive strength.

In order to address the above problems many researchers have tried to change the physical properties of cyanoacrylate, but the results have not been successful. Therefore, it is necessary to develop a bioaffinity cyanoacrylate having improved adhesive strength not using a low-molecular plasticizer and an artificial reactive adhesive thereof.

Given this situation, the inventors have confirmed that a bioadhesive composition having more powerful adhesive strength to an adherent and a low toxicity can be provided by preparing a bioadhesive composition having a structure in which at least one of a double bond in a molecule remains at the site adjacent to a cyano group prepared by causing prepolymerization in a double bond moiety of an allyl group by pre-polymerizing heating 2-cyanoacrylate having at least two double bonds in a molecule such as an allyl 2-cyanoacrylate, thereby completing the present invention.

SUMMARY OF THE INVENTION

An object of the present invention is to provide a modified allyl 2-cyanoacrylate obtained by pre-polymerizing through heating an allyl 2-cyanoacrylate.

Another object of the present invention is to provide a method for preparing the modified allyl 2-cyanoacrylate.

Still another object of the present invention is to provide a bioadhesive composition including the modified allyl 2-cyanoacrylate.

DETAILED DESCRIPTION OF THE INVENTION

In order to achieve the above objects, an exemplary embodiment of the present invention provides a compound represented by the following Chemical Formula 1:

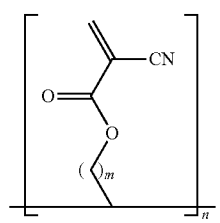

[Chemical Formula 1]

wherein, n represents an integer between 2 to 1000; and m represents an integer between 1 to 20.

Preferably, the n is an integer between 10 to 100.

Preferably, the m is an integer between 1 to 5.

Preferably, a molecular weight of the compound represented by the above Chemical Formula 1 is 1,000 to 1,000,000.

Preferably, a viscosity of the compound represented by the above Chemical Formula 1 is 80 mPa·s to 400 mPa·s.

In addition, the present invention provides a method for preparing a compound represented by the following Chemical Formula 1, the method including the step of:

preparing a compound represented by the following Chemical Formula 1 by pre-polymerizing through heating a compound represented by the following Chemical Formula 2:

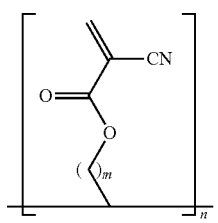
[Chemical Formula 1]

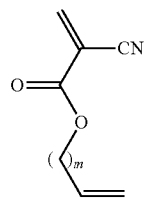
[Chemical Formula 2]

wherein, n represents an integer between 2 to 1000; and m represents an integer between 1 to 20.

Preferably, the n is an integer between 10 to 100.

Preferably, the m is an integer between 1 to 5.

Preferably, a molecular weight of the compound represented by the above Chemical Formula 1 is 1,000 to 1,000,000.

Preferably, a viscosity of the compound represented by the above Chemical Formula 1 is 80 mPa·s to 400 mPa·s.

The Step 1 is a step for preparing the compound represented by Chemical Formula 1 by pre-polymerizing through heating the compound represented by Chemical Formula 2.

Conventionally, a bioadhesive 2-cyanoacrylate is polymerized in a double bond moiety that is adjacent to a cyano group by an anionic polymerization, thereby obtaining a bioadhesive 2-cyanoacrylate polymer compound having a structure lacking a double bond in a molecule. In addition, in the case of polymerization of a 2-cyanoacrylate having at least two double bonds in a molecule, such as an allyl 2-cyanoacrylate, polymerization is caused in a double bond moiety that is adjacent to a cyano group by an anionic polymerization, and subsequently, polymerization is again caused in a double bond moiety of an allyl group through heating to obtain a bioadhesive 2-cyanoacrylate polymer compound having a structure lacking a double bond in a molecule.

However, the present invention can prepare a bioadhesive compound represented by Chemical Formula 1 having a structure in which one double bond in a molecule remains at the site adjacent to a cyano group by causing pre-polymerization in a double bond moiety of an allyl group by way of performing a pre-polymerization through heating. The compound having such a structure can achieve the effect of protecting the wound by a sudden polymerization effect of the 2-cyanoacrylate through a double bond that is adjacent to a cyano group, in which the double bond remains after application on the skin for use as a bioadhesive. In addition, pre-polymerization is performed at a double bond site of an allyl group such that an alkyl chain of the 2-cyanoacrylate becomes longer, thereby achieving the effect of decreasing toxicity. In addition, the heating temperature and heating time are controlled during pre-polymerizing, so that the viscosity of the bioadhesive 2-cyanoacrylate produced can be easily controlled.

In the present invention, the heating in Step 1 is preferably performed at 50° C. to 200° C. If the heating temperature is not within the range described above, there are disadvantages in that the pre-polymerization is not completed or a side reaction is caused.

In the present invention, the heating of Step 1 is preferably performed for 3 seconds to 2 hours. When the heating time is not within the range described above, there are disadvantages in that the pre-polymerization is not completed or a side reaction is caused.

In addition, the present invention is to provide a bioadhesive composition including a compound represented by the Chemical Formula 1 described above.

The term, "bioadhesive" used in the present invention means a material for inducing an adhesion between two biological materials. The bioadhesive of the present invention is a bioadhesive based on a cyanoacrylate. The bioadhesive of the present invention can be used, for example, as a bioadhesive for dentistry or medical care and especially as a bioadhesive for soft tissues as for a dental adhesive or as an adhesive for inosculation of blood vessels and living body tissues, and as means of reversing damage or incisions due to surgery as for a medical adhesive.

In conventional bioadhesives, inflammations caused by the components of the bioadhesive permeating into the wound, rather weak adhesive strength in comparison with a coating film having a hard property, repulsion due to differences in physical properties with skin, and the like have risen as representative problems. The bioadhesive composition of the present invention is based on a 2-cyanoacrylate compound represented by Chemical Formula 1 described above, with one double bond in a molecule. The bioadhesive composition of the present invention provides protective effects around the wound, such as a significant decrease in side reaction, for example of inflammation and the like, by inhibiting permeation of adhesive components inside the wound by a sudden polymerization effect through a double bond present in the 2-cyanoacrylate, and additionally exhibits improved adhesive strength. In addition, the bioadhesive composition of the present invention has an advantage in that toxicity can be decreased by using the 2-cyanoacrylate having an extended alkyl chain by pre-polymerizing at a double bond site of an allyl group. Furthermore, the bioadhesive composition of the present invention can cover the area around the wound and exhibit effective treatment thereof on the wound, and in some cases, can be used as a matrix for the isolation of medical compounds. In addition, since the components used for the bioadhesive composition of the present invention are easily obtained at a low cost, a bioadhesive composition having economic efficiency can be provided.

Effect of the Invention

The present invention has an effect of providing a bioadhesive composition having more powerful adhesive strength to an adherent and low toxicity, by preparing a bioadhesive composition having structure in which at least one double bond in a molecule remains at the site adjacent to a cyano group prepared by causing pre-polymerization in a double bond moiety of an allyl group by pre-polymerizing through heating 2-cyanoacrylate having at least two double bonds in a molecule, such as an allyl 2-cyanoacrylate, thereby completing the present invention.

DETAILED DESCRIPTION OF THE PREFERRED EMBODIMENTS

Hereinafter, the present invention will be described in more detail with reference to Examples. The Examples are only for describing the present invention in greater detail, and the scope of the present invention is not intended to be limited to the Examples.

EXAMPLE 1

10 ml of an allyl 2-cyanoacrylate was added to a glass test tube and then sealed in a vacuum state. The sealed glass test tube was put in an oil bath of 150° C. to heat it for 5, 10, 20, 30, 40, 50, 60, and 70 minutes. The heated cyanoacrylate per each given period of time was cooled at room temperature and then the change in viscosity was observed.

EXAMPLE 2

An allyl 2-cyanoacrylate was heated; then the heated cyanoacrylate per each given period of time was cooled at room temperature, and then the change in viscosity was observed, by using an identical method as described in Example 1 above, with the exception that the temperature of the oil bath was set to 100° C.

COMPARATIVE EXAMPLE 1

An ethyl 2-cyanoacrylate was heated; then the heated cyanoacrylate per each given period of time was cooled at room temperature, and then the change in viscosity was observed, by using an identical method as in Example 1 described above, with the exception that ethyl 2-cyanoacrylate was used instead of allyl 2-cyanoacrylate.

EXPERIMENTAL EXAMPLE 1

Figure 1:
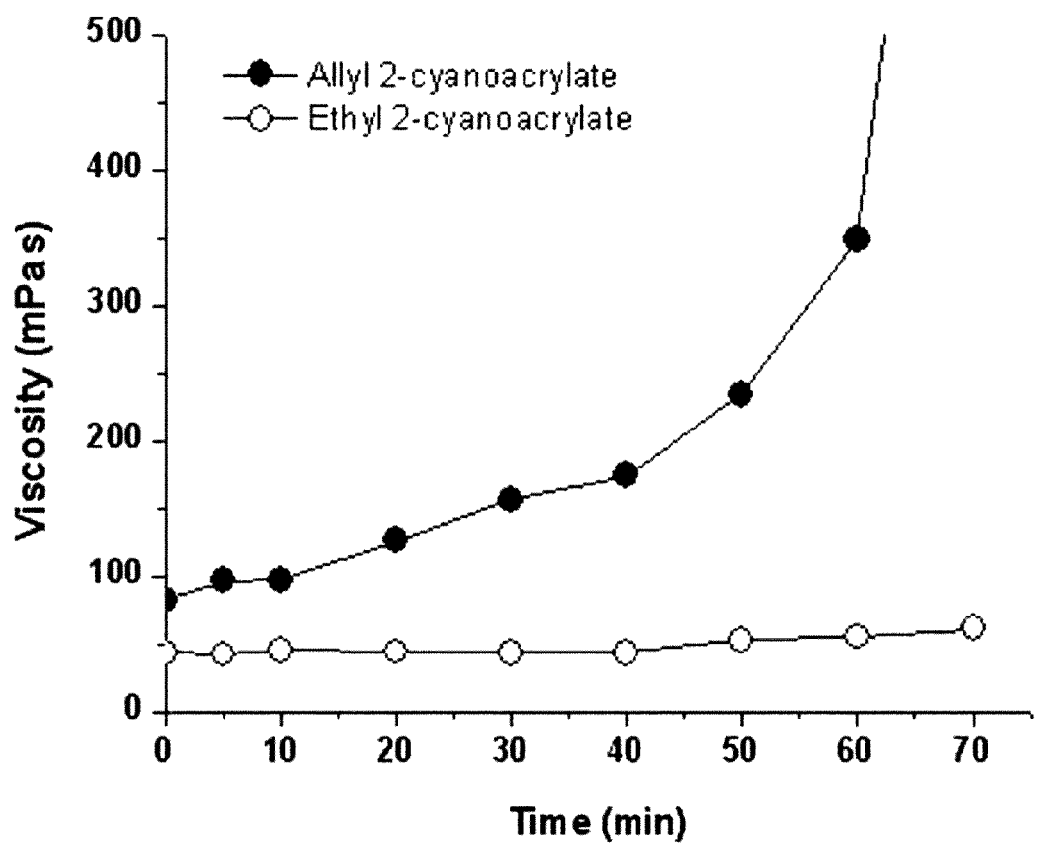
FIG. 1 is a graph illustrating a result of investigating a change of the viscosity relative to the time of heating 2-cyanoacrylate prepolymers in Example 1 and Comparative Example 1.

Investigation of Change of Viscosity According to Time for Heating 2-cyanoacrylate Prepolymer According to the Present Invention The results of investigating the change in viscosity according to time of heating the 2-cyanoacrylate prepolymer in Example 1 and Comparative Example 1 are shown in FIG. 1. Furthermore, the values of viscosity according to time of heating the 2-cyanoacrylate prepolymer in Example 1 are shown in the following Table 1.

TABLE 1

| Time (Minutes) | Viscosity (mPa · s) |
| --- | --- |
| 0 | 82 |
| 5 | 96 |
| 10 | 97 |
| 20 | 126 |
| 30 | 156 |
| 40 | 174 |

TABLE 1-continued

| Time (Minutes) | Viscosity (mPa · s) |
| --- | --- |
| 50 | 234 |
| 60 | 384 |

As illustrated in Table 1 and FIG. 1, it could be confirmed that the viscosity of the 2-cyanoacrylate prepolymer of the present invention increased with greater heating time. On the other hand, as illustrated in FIG. 1, it could be confirmed that there was no increase in the viscosity with greater heating time in the ethyl 2-cyanoacrylate having one double bond in a molecule. From the above results, it could be confirmed that pre-polymerization was not the polymerization occurring at a double bond adjacent to a cyano group involved in an anionic polymerization, but rather the polymerization reaction occurring at a double bond of an allyl group.

EXPERIMENTAL EXAMPLE 2

Investigation of Adhesive Strength of 2-cyanoacrylate Prepolymer According to the Present Invention The adhesive strength of 2-cyanoacrylate prepolymer as prepared by heating for 5 minutes in Example 1 was investigated. Additionally as a control group, ethyl 2-cyanoacrylate of Comparative Example 1 was used.

Figure 2:
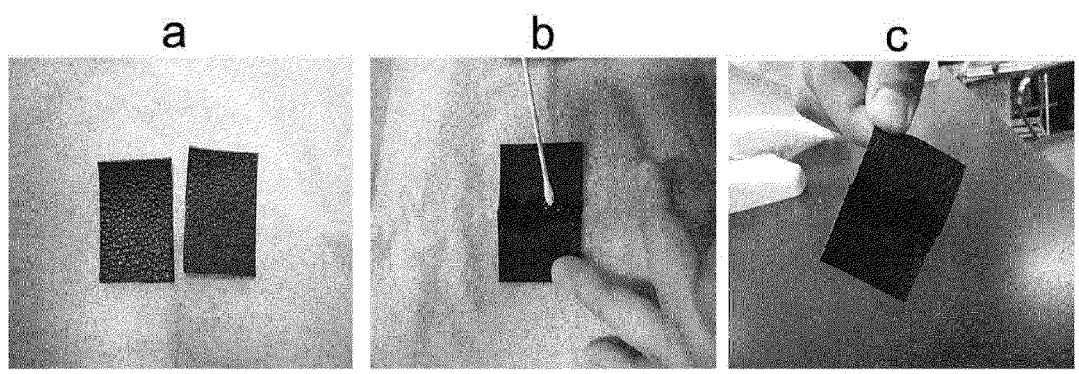
FIG. 2 is a photograph diagram illustrating a process for testing adhesive strength of the 2-cyanoacrylate prepolymers of the present invention.

For testing adhesive strength, as illustrated in FIG. 2, the skin of a cow was cut to 2.5 cm wide and 5 cm long (a); then an adhesive was applied on an area with a length and width of 1 cm each on the cut skin of the cow (b); after the skin was stacked, this state thereof was maintained for 3 minutes (c); and then the skin was pulled at a rate of 1 mm/min until it tore to measure adhesive strength. The results are shown in FIG. 3.

Figure 3:
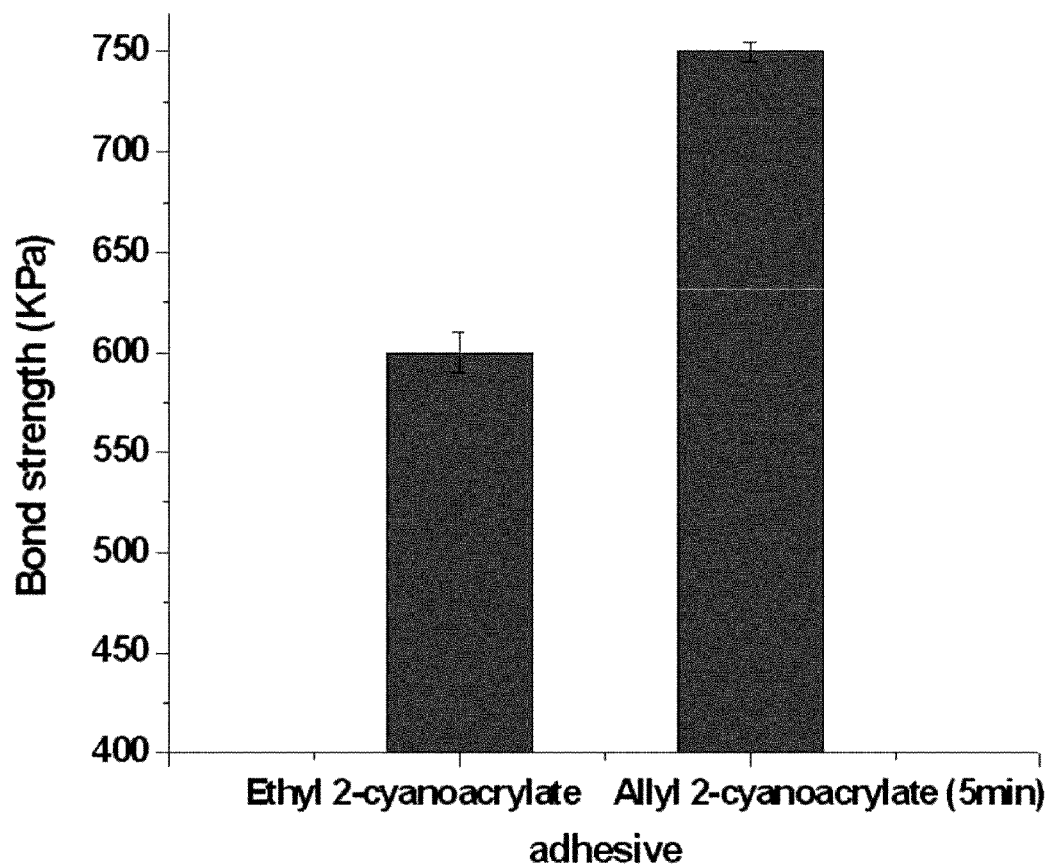
FIG. 3 is a graph illustrating a result of testing adhesive strength of the 2-cyanoacrylate prepolymers of the present invention.

As illustrated in FIG. 3, in the case of using the 2-cyanoacrylate prepolymer prepared in Example 1, adhesive strength was increased as compared with the control group using the ethyl 2-cyanoacrylate used in Comparative Example 1.

What is claimed is:

1. A compound represented by the following Chemical Formula 1:

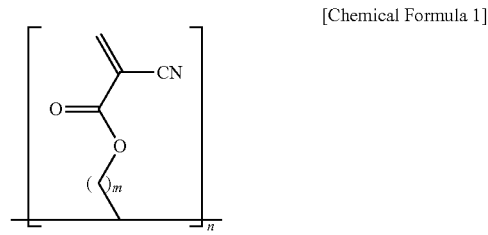

[Chemical Formula 1]

wherein,
n represents an integer between 2 to 1000; and
m represents an integer between 1 to 20.

2. The compound according to claim 1, wherein the n represents an integer between 10 to 100.

3. The compound according to claim 1, wherein the m represents an integer between 1 to 5.

4. The compound according to claim 1, wherein a viscosity of the compound represented by the Chemical Formula 1 is 80 mPa·s to 400 mPa·s.

5. A bioadhesive composition comprising the compound according to any one of claims 1 to 3 and 4.

6. A method for preparing a compound represented by the following Chemical Formula 1, the method comprising:
preparing the compound represented by the following Chemical Formula 1 by pre-polymerizing through heating a compound represented by the following Chemical Formula 2 in a vacuum state:

[Chemical Formula 1]

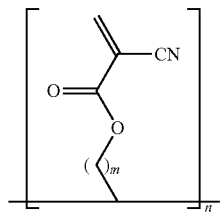

[Chemical Formula 2]

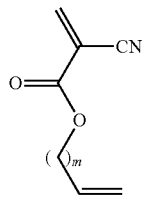

wherein, n represents an integer between 2 to 1000; and m represents an integer between 1 to 20.

7. The method according to claim 6, wherein the heating is performed at 50° C. to 200° C.

8. The method according to claim 6, wherein the heating is performed for 3 seconds to 2 hours.

* * * * *